(12) United States Patent
Barzilai et al.

(10) Patent No.: US 9,347,963 B2
(45) Date of Patent: *May 24, 2016

(54) APPARATUS AND METHOD FOR TRANSPORTING SAMPLE WELL TRAYS

(75) Inventors: Jessica E. Barzilai, Alexandria, VA (US); Donald R. Sandell, San Jose, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/091,773

(22) Filed: Apr. 21, 2011

(65) Prior Publication Data

US 2011/0300622 A1 Dec. 8, 2011

Related U.S. Application Data

(63) Continuation of application No. 10/785,082, filed on Feb. 25, 2004, now abandoned, which is a continuation of application No. 09/606,006, filed on Jun. 29, 2000, now Pat. No. 6,719,949.

(51) Int. Cl.
| | |
|---|---|
| *G01N 33/00* | (2006.01) |
| *G01N 35/04* | (2006.01) |
| *B01L 9/00* | (2006.01) |
| *G01N 35/02* | (2006.01) |

(52) U.S. Cl.
CPC ............... *G01N 35/04* (2013.01); *B01L 9/523* (2013.01); *B01L 2300/0829* (2013.01); *G01N 35/028* (2013.01); *G01N 2035/042* (2013.01); *Y10T 436/11* (2015.01)

(58) Field of Classification Search
CPC ................................ G01N 35/04; B01L 9/523
See application file for complete search history.

(56) References Cited

U.S. PATENT DOCUMENTS

| | | |
|---|---|---|
| 3,080,759 A | 3/1963 | McQuaid |
| 3,933,165 A | 1/1976 | Budzak et al. |
| 4,407,570 A | 10/1983 | Hayasaka |
| 4,948,564 A | 8/1990 | Root et al. |
| 4,981,801 A | 1/1991 | Suzuki |

(Continued)

FOREIGN PATENT DOCUMENTS

| | | |
|---|---|---|
| DE | 19739119 | 3/1999 |
| EP | 0895240 | 2/1999 |

(Continued)

OTHER PUBLICATIONS

Grossman, et al., High-Density Multiplex Detection of Nucleic Acid Sequences: Oligonucleotide Ligation Assay and Sequence-Coded Separation, Nucleic Acids Research, 22(21), 1984, 4527-4534.

(Continued)

*Primary Examiner* — Sam P Siefke (57) ABSTRACT

An apparatus for transporting sample well trays with respect to a heating device is provided. The apparatus includes a sample well tray holder, a rotational actuator, and a biasing mechanism. The sample well tray holder includes a plate in which a sample well tray may be positioned. The sample well tray holder is configured to rotate about a first rotational axis. The rotational actuator is configured to rotate the sample well tray holder about the first rotational axis. The biasing mechanism is configured to urge the sample well tray holder in a generally upward direction along the first rotational axis.

16 Claims, 8 Drawing Sheets

(56) References Cited

U.S. PATENT DOCUMENTS

| | | |
|---|---|---|
| 5,149,654 A | 9/1992 | Gross |
| 5,210,015 A | 5/1993 | Gelfand et al. |
| 5,233,844 A | 8/1993 | Knippscheer |
| 5,455,008 A * | 10/1995 | Earley et al. .................. 422/511 |
| 5,525,300 A | 6/1996 | Danssaert et al. |
| 5,538,848 A | 7/1996 | Livak et al. |
| 5,780,717 A | 7/1998 | Wise et al. |
| 5,928,907 A | 7/1999 | Woudenberg et al. |
| 5,955,373 A | 9/1999 | Hutchins |
| 6,015,674 A | 1/2000 | Woudenberg et al. |
| 6,054,263 A | 4/2000 | Danssaert et al. |
| 6,099,230 A | 8/2000 | Hitch |
| 6,159,368 A | 12/2000 | Moring et al. |
| 6,272,939 B1 | 8/2001 | Frye et al. |
| 6,323,035 B1 | 11/2001 | Kedar et al. |
| 6,340,589 B1 | 1/2002 | Turner et al. |
| 6,343,906 B1 | 2/2002 | Kraemer et al. |
| 6,448,066 B1 | 9/2002 | Wheatcroft |
| 6,569,620 B1 | 5/2003 | Gold et al. |
| 6,656,724 B1 | 12/2003 | Heimberg et al. |
| 6,719,949 B1 | 4/2004 | Barzilai et al. |
| 7,169,355 B1 * | 1/2007 | Shin et al. ....................... 422/63 |

FOREIGN PATENT DOCUMENTS

| | | |
|---|---|---|
| EP | 0955097 | 11/1999 |
| EP | 1088590 | 4/2001 |
| GB | 2343873 | 9/2002 |
| JP | 9-510863 | 11/1997 |
| JP | 2001-194372 | 7/2001 |
| WO | 91/17239 | 11/1991 |
| WO | 97/36681 | 10/1997 |
| WO | 01/28684 | 4/2001 |
| WO | 02/02235 | 1/2002 |

OTHER PUBLICATIONS

Landegren, U. et al., A Ligase-Mediated Gene Detection Technique, Science, 241, 1988, 1077-1080.

Nickerson, D. et al., Automated DNA diagnostics using an ELISA-based oligonucleotide ligation assay, Proc. Natl. Acad. Sci. USA, 87, Nov. 1990, 8923-8927.

International Search Report for International Application No. PCT/US01/20459 mailed May 28, 2002.

* cited by examiner

APPARATUS AND METHOD FOR TRANSPORTING SAMPLE WELL TRAYS

CROSS-REFERENCE TO RELATED APPLICATIONS

This application is a continuation of U.S. patent application Ser. No. 10/785,082 filed Feb. 25, 2004, which is a continuation of U.S. patent application Ser. No. 09/606,006 filed Jun. 29, 2000, all of which are incorporated herein by reference.

BACKGROUND OF THE INVENTION

1. Field of the Invention

The present invention relates to an apparatus and method for transporting sample well trays. In certain embodiments, the apparatus places sample well trays into a heating device and removes the sample well trays therefrom.

2. Description of the Related Art

Biological testing has become an important tool in detecting and monitoring diseases. In the biological testing field, thermal cycling is often utilized in order to amplify nucleic acids by, for example, performing polymerase chain reactions (PCR) and other reactions.

It is desirable to increase the throughput of such biological testing. One method for increasing throughput is to provide real-time detection capability during thermal cycling. Providing real-time detection increases the efficiency of the biological testing because the samples can be tested while in the thermal cycling device, therefore not requiring removal of the sample well tray prior to testing the samples. An additional method of increasing throughput of biological testing is to automatically load sample well trays into the heating device, perform a heating operation such as thermal cycling, and then automatically remove the sample well tray using a robotic mechanism. However, existing robotic mechanisms are not particularly suited for thermal cycling devices with real-time detection units. In particular, existing robotic mechanisms are not particularly configured for accessing the thermal cycling device without interfering with the detection units.

It is desirable to provide a sample well tray manipulating apparatus and method that is compatible for use with thermal cycling devices having real-time detection units in order to increase throughput.

SUMMARY OF THE INVENTION

The advantages and purposes of the invention will be set forth in part in the description which follows, and in part will be apparent from the description, or may be appreciated by practice of the invention. The advantages and purposes of the invention will be realized and attained by means of the elements and combinations particularly pointed out in the appended claims. In one aspect, the invention includes an apparatus for transporting sample well trays with respect to a heating device. In certain embodiments, the apparatus includes a sample well tray holder, a rotational actuator, and a biasing mechanism. The sample well tray holder includes a plate in which a sample well tray may be positioned. The sample well tray holder is configured to rotate about a first rotational axis. The rotational actuator is configured to rotate the sample well tray holder about the first rotational axis. The biasing mechanism is configured to urge the sample well tray holder in a generally upward direction along the first rotational axis.

In another aspect, the invention includes a robotic manipulator for transporting sample well trays between at least two positions. The robotic manipulator includes a robotic arm, a rotational mechanism, and a biasing mechanism. The robotic arm includes a sample well tray holder configured to support a sample well tray therein. The sample well tray holder includes a recess for the sample well tray. The rotational mechanism is configured to impart rotational motion on the robotic arm, and includes a motor. The biasing mechanism is configured to provide force on the sample well tray holder in a direction away from an adjacent sample block.

In a further aspect, the invention includes a system for manipulating sample well trays. The system includes a robot configured to transport a sample well tray to a first location, a loading mechanism, and a heating device. The loading mechanism is configured to take a sample well tray from the first location, place the sample well tray into the heating device, for example, a thermal cycler at a second location and then later remove the sample well tray from the heating device and return the sample well tray to the first location. The loading mechanism includes a sample well tray holder in which a sample well tray may be positioned therein, a rotational actuator configured to rotate the sample well tray holder, and a biasing member configured to urge the sample well tray and sample well tray holder in a direction away from a sample block. The heating device includes an opening for receiving the sample well tray therein.

In yet another aspect, the invention includes a method of manipulating sample well trays. The method includes the step of placing the sample well tray into a sample well tray holder of a first robot mechanism located at a first position. The method further includes the step of rotating the sample well tray holder of the first robot mechanism about a rotational axis in a first rotational direction to insert the sample well tray holder into a heating device at a second position. The sample well tray holder is lowered in a direction toward a sample block of the heating device so that the sample well tray engages the sample block. After undergoing thermal cycling or other operations, the sample well tray disengages from the sample block so that the sample well tray does not directly contact the sample block. The method further includes lifting the sample well tray holder and sample well tray from the heating device by a biasing mechanism so that the sample well tray is capable of rotation away from the sample block and heating device without interference, and then rotating the sample well tray holder of the first robot mechanism in a second rotational direction toward the first position to remove the sample well tray holder from the heating device. The sample well tray may then be removed from the sample well tray holder. The method further includes, prior to placing the sample well tray in a sample well tray holder, the steps of picking up a sample well tray with a second robot mechanism, such as a rotational robot, and rotating the sample well tray to place the sample well tray in the first position.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

In accordance with the present invention, an apparatus for transporting sample well trays with respect to a heating device is provided. In certain embodiments of the present invention, the apparatus includes a sample well tray holder, a rotational actuator configured to rotate the sample well tray holder, and a biasing mechanism configured to urge the sample well tray holder in a generally upward direction. In certain embodiments, the invention is directed toward a system which additionally includes a robot device for transporting a sample well tray to the sample well tray holder, and a heating device with an opening for receiving the sample well tray therein. As embodied herein and shown in FIGS. 1-9, the handling apparatus 10 for transporting sample well trays includes a sample well tray holder 12, a rotational actuator 14, and a biasing mechanism 16.

Figure 5:
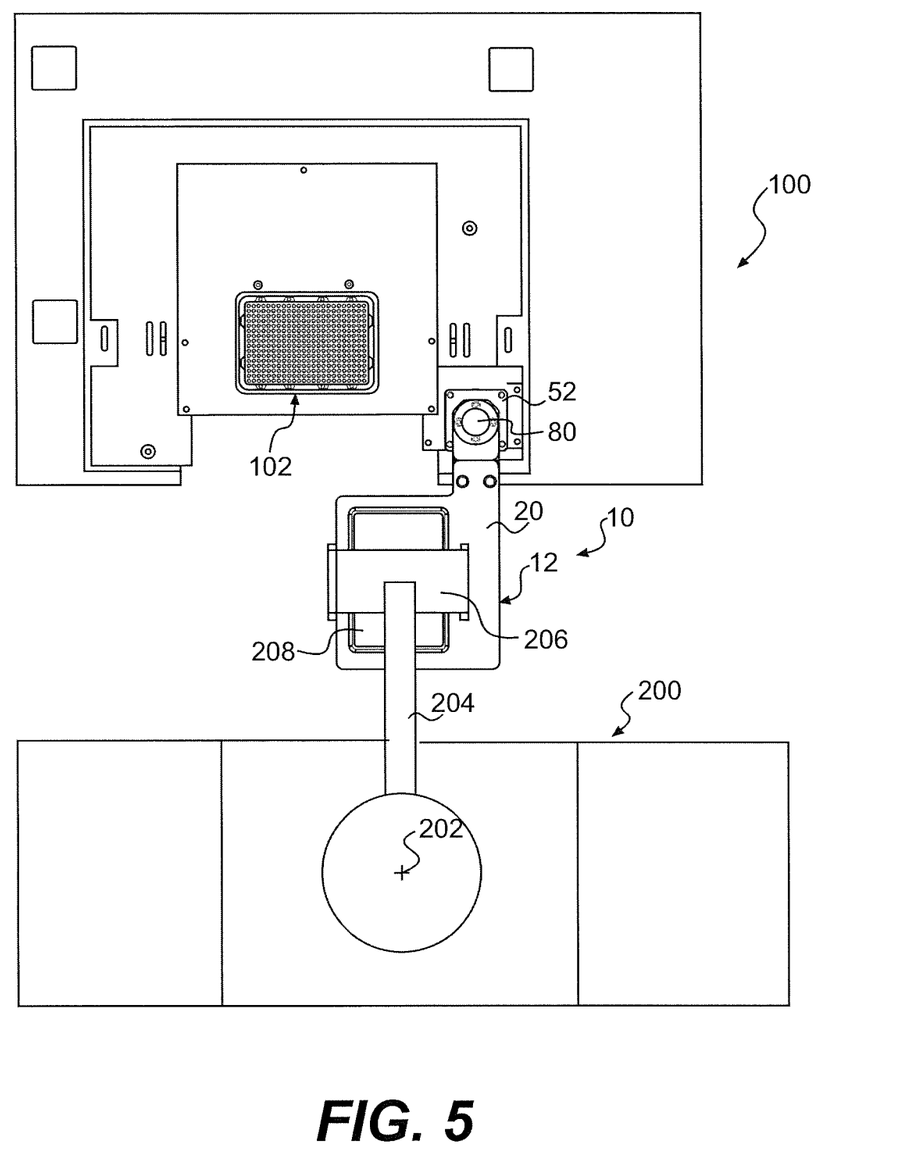
FIG. 5 shows a top view of a system including the sample well tray handling apparatus of FIG. 1 in addition to a heating device and a robot, the sample well tray handling apparatus in a first position for having a sample well tray transferred from the robot.
Figure 6:
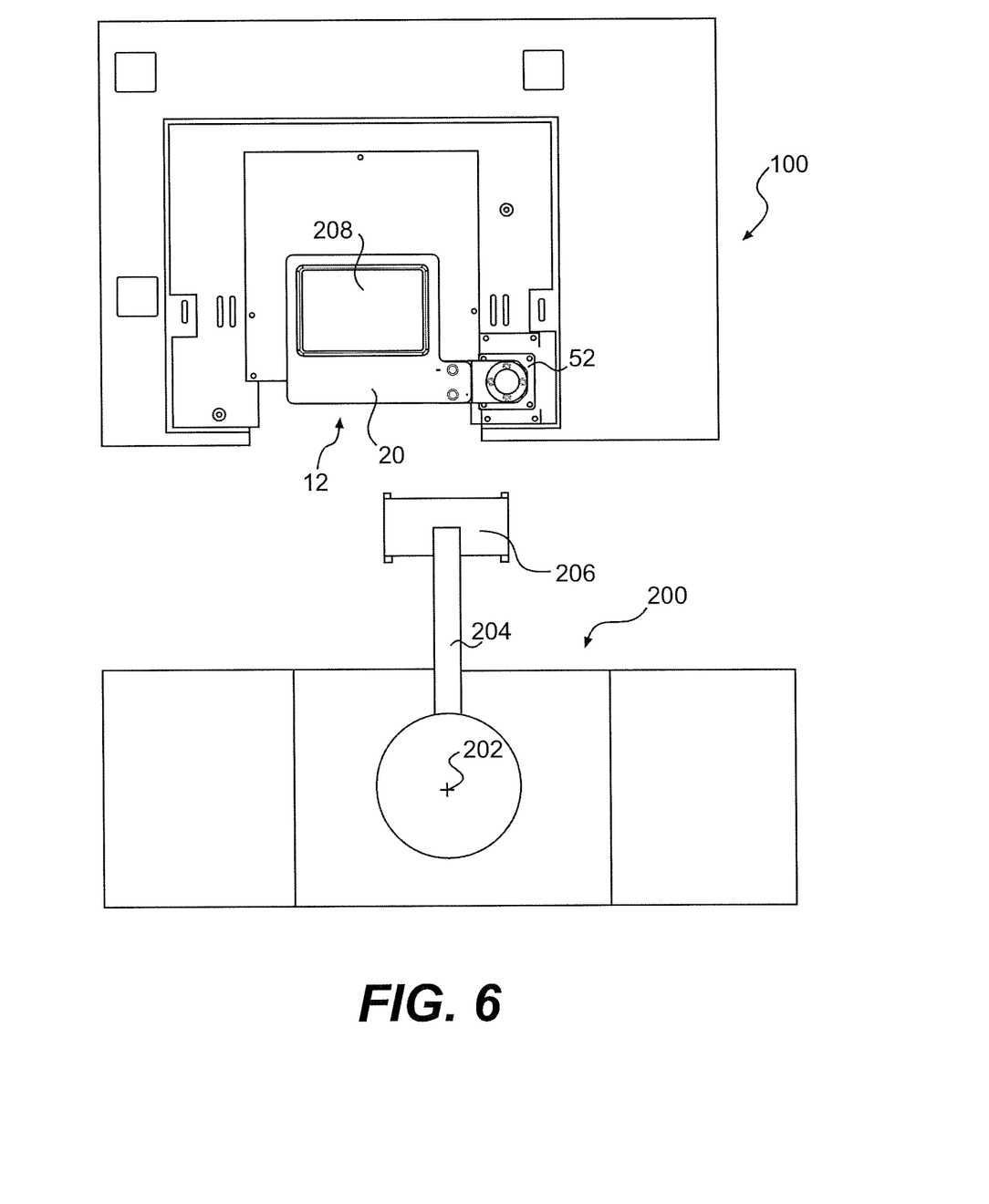
FIG. 6 shows a top view of the system of FIG. 5, the sample well tray handling apparatus rotated relative to the first position of FIG. 5 so that the sample well tray is located in the heating device.
Figure 9A:
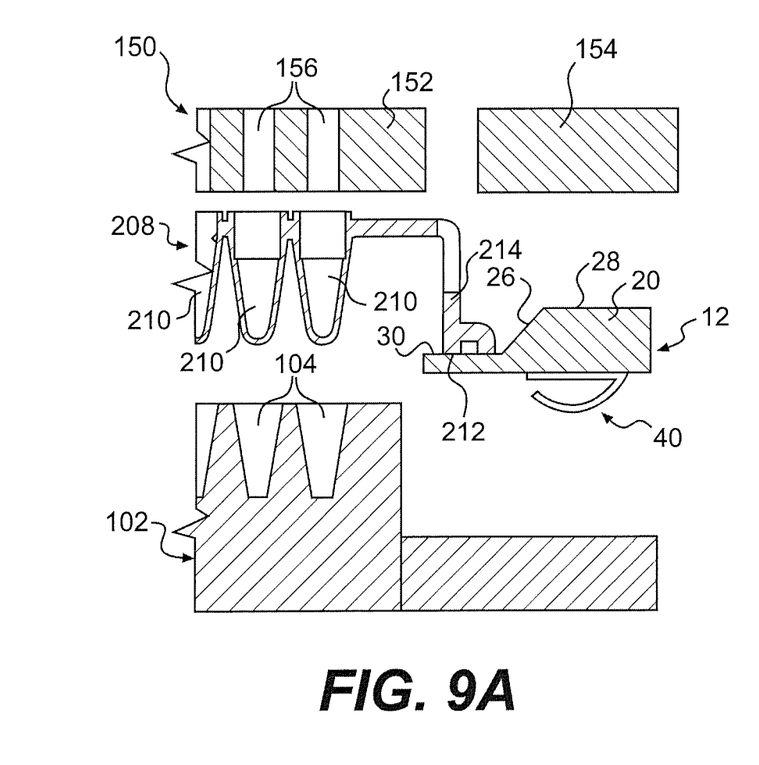
FIG. 9A is a schematic sectional view illustrating a cover and sample well tray in an open position.
Figure 9B:
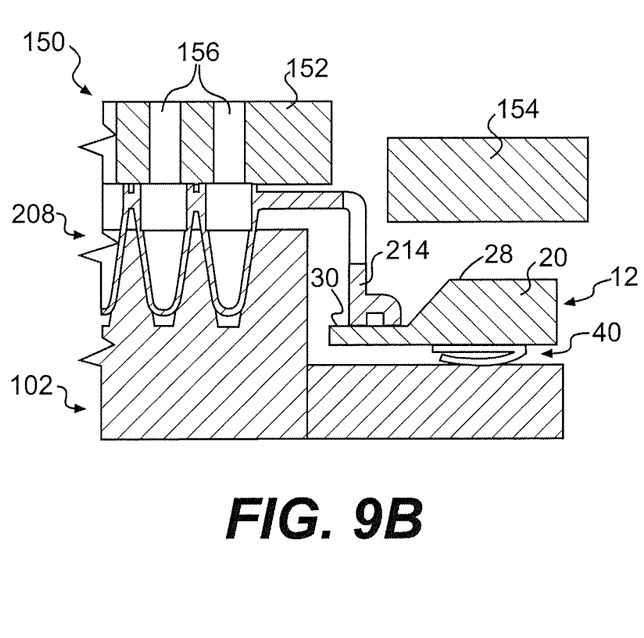
FIG. 9B is a schematic sectional view illustrating the cover and sample well tray of FIG. 9A in a closed position.

Handling apparatus 10 may be used to load and unload sample well trays into a wide variety of types of heating devices. In certain embodiments, the heating device may be a PE Biosystems 5700 and 7700 Detection Instrument, as well as a variety of other types of instruments. One example of a suitable heating device is described in U.S. Pat. No. 5,928,907 to Woudenberg et al., which is assigned to the assignee of the present invention, the contents of which are hereby incorporated by reference herein for any purpose. The heating device 100 shown in FIGS. 5-6 is preferably configured for use with 96-well and 384-well sample trays, in addition to microcard sample trays. One example of a 384-well sample tray is illustrated in FIGS. 9A and 9B as a sample well tray 208 with a plurality of sample wells 210. Examples of sample well trays suitable for use in the apparatus of the present invention are described in WO00/25922 to Moring et al., which is assigned to the assignee of the present invention, the contents of which are hereby incorporated by reference herein for any purpose. Examples of microcard sample trays suitable for use in the apparatus of the present invention are described in WO97/36681 to Woudenberg et al., which is assigned to the assignee of the present invention, the contents of which are hereby incorporated by reference herein for any purpose. Sample well trays having any number of sample wells and sample well sizes may also be used. In the example shown in the figures, the volume of the sample wells may vary anywhere from 0.01 µl to thousands of microliters (µl), with a volume between 10 to 500 µl being typical. The detection instrument may be used for a variety of applications, such as, but not limited to, fluorescent PCR-based detection.

As embodied herein and shown in FIGS. 5, 6, 9A, and 9B, the heating device 100 includes a sample block 102 or other type of surface for receiving a sample well tray, such as sample well tray 208, from the handling apparatus 10. As shown in FIGS. 5, 6, 9A, and 9B, sample block 102 includes a plurality of openings 104 in a top portion thereof for receiving sample wells 210 of the sample well tray. Each of the sample block openings 104 may have a conical shape which is sized to fit with a sample well of a sample well tray. The sample block openings may be other shapes such as cylindrical or hemispherical, depending on the shape of the mating sample wells. Sample blocks are well known in the art. The sample block will typically have openings of a number matching the number of sample wells of the sample well tray.

The sample block shown in FIG. 5 has 384 openings arranged in a 16×24 array, however, any number of openings may be provided. Other common configurations include 96 and 60-well sample blocks, although the present invention is suitable for sample well trays having anywhere from one sample well to several thousand sample wells. The sample block is preferably constructed of a heat-conducting material such as gold-plated silver and aluminum, although other common materials may also be suitable.

Likewise, although the description discusses trays with sample wells, the present invention is suitable for use with sample trays that do not include wells. These trays may have a flat surface on which a sample of biological material is placed. The flat surface on which the sample is placed may be similar to a microscope slide for a sample. In this type of sample tray, a liquid may be dropped onto the tray at a plurality of positions, and then a film or cover positioned on the top surface of the tray over the samples. Alternately, a sample tray may include a porous material such a frit on the top surface, instead of sample wells, for holding samples of biological material. Therefore, although the description refers to sample well trays throughout, it should be understood that the present invention is also suitable for sample trays that do not have sample wells.

The heating device 100 further includes a cover which lowers and applies pressure to the top of the sample well tray after the sample well tray is inserted into the heating device. In an exemplary embodiment shown in FIGS. 9A and 9B, a heated cover 150 includes a central cover portion 152 and an outer cover portion 154. In the embodiment shown in FIGS. 9A and 9B, the central cover portion 152 has a plurality of openings 156 for the optical detection of reactions that occur in the sample wells of the sample well tray. The present invention is also suitable for use in a thermal cycler or other heating apparatus without optical detection capabilities. In one embodiment, the outer cover portion 154 is movable in an upward and downward direction relative to the central cover portion 152. The cover may be any of a variety of types. For example, in certain embodiments, the cover is physically actuated to and from a closed position by a motor. In other embodiments, the cover is slid into and out of a closed position by manual physical application. The cover may also include at least one heated platen (not shown) for pressing against the top surface of the sample well trays in order to reduce condensation from occurring on the sample well trays.

The handling apparatus 10 may receive the sample well trays either manually or automatically. In certain embodiments, the handling apparatus 10 receives sample well trays from a robot, such as robot 200 shown in FIGS. 5 and 6. The robot 200 may be any type of robot, such as a rotational robot that rotates about a single axis 202. One example of a rotational robot that is suitable for use with the handling apparatus 10 is a Zymark™ Twister robot. In certain embodiments, the robot 200 includes an arm 204 and a robot hand 206 for gripping a sample well tray 208. The rotational robot picks up a single sample well tray 208 and then rotates about the rotational axis 202 to bring the sample well tray to the position shown in FIG. 5. In the position shown in FIG. 5, the sample well tray 208 may be transferred to handling apparatus 10. The handling apparatus 10 then inserts the sample well tray into sample block 102 of heating device 100 as shown in FIG. 6 and the samples in the sample well tray are thermally cycled. The handling apparatus removes the sample well tray from the heating device and rotates back to FIG. 5 so that the sample well tray may be picked up from the handling apparatus by the robot 200. The heating device may be any type known in the art. The specific heating devices discussed in relation to the present invention are described for purposes of illustration only.

The present invention is directed at the handling apparatus, as well as the overall system. In accordance with the present invention, the handling apparatus 10 includes a sample well tray holder 12 for supporting a sample well tray therein. As embodied herein and shown in FIGS. 1-4, the sample well tray holder 12 is in the shape of a flat plate with a main body portion 20 and an arm portion 22. In the example shown in the figures, the main body portion 20 is in a rectangular shape. The main body portion 20 defines a rectangular opening or recess 24 sized and shaped for receiving a sample well tray. The sample well tray holder is preferably made out of a material with poor heat conduction characteristics and a low thermal mass. In certain embodiments, the material selected for the sample well tray holder is a polycarbonate. Other suitable materials are also acceptable, including a hybrid metal/plastic sample tray holder.

The rectangular opening 24 of the sample well tray holder is configured so that the sample well tray 208 may rest on the sample well tray holder. The rectangular opening 24 is defined by a tapered wall 26 which tapers downward from the top surface 28 of the sample well tray holder 12. The tapered wall 26 tapers until it meets a floor portion 30 which extends from the tapered wall. The floor portion 30 generally extends along a bottom surface of the sample well tray holder. The floor portion 30 defines a rectangular opening that is smaller than the size of a sample well tray. Therefore, when a sample well tray is placed in the rectangular opening 24, a bottom surface 212 of outer side walls 214 of the sample well tray 208 rest on a top surface of the floor portion 30, as best illustrated in FIG. 9A. The provision of the tapered wall 26 permits the sample well tray 208 to center itself in the rectangular opening 24 as the sample well tray is placed in the rectangular opening.

Figure 1:
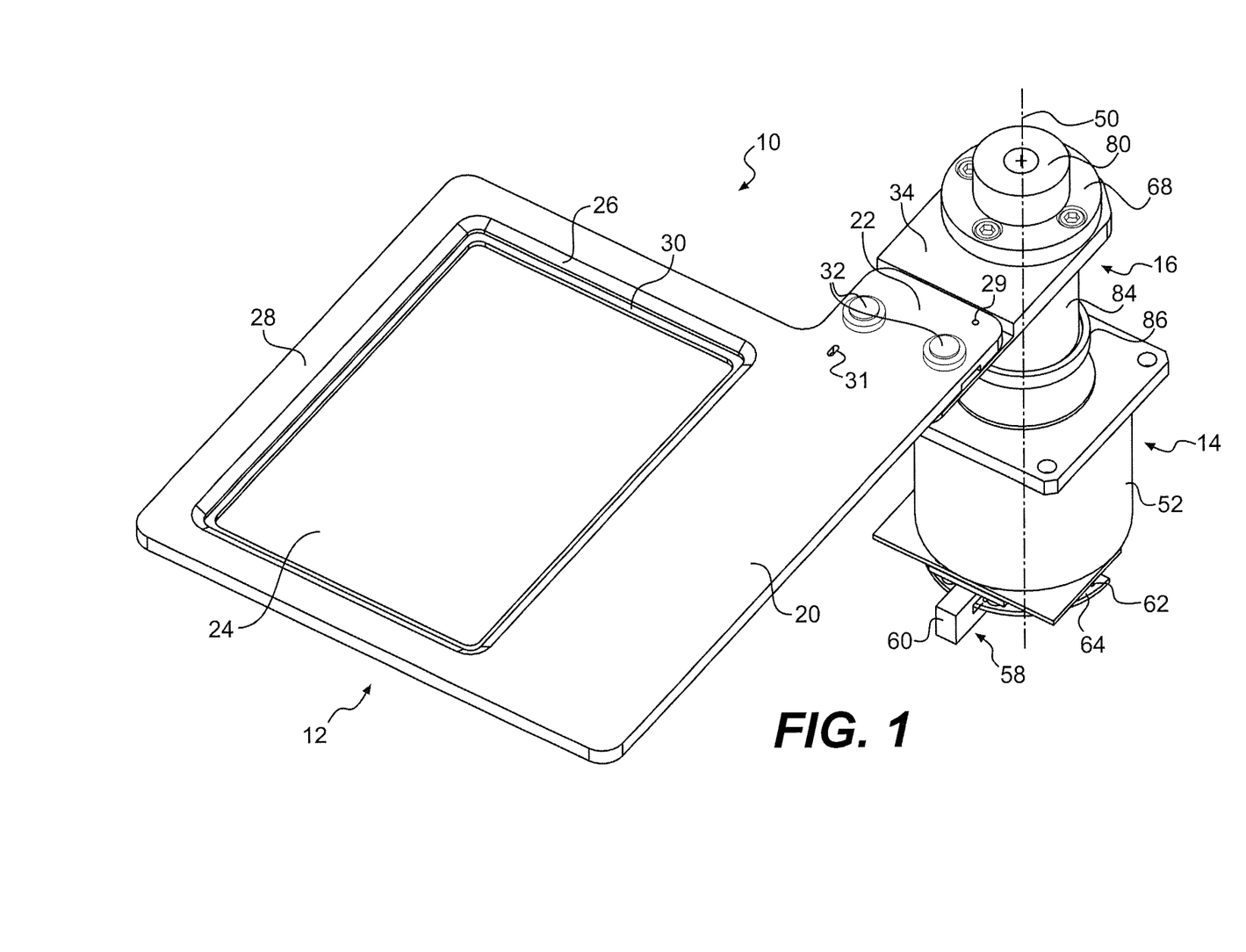
FIG. 1 shows a perspective view of a sample well tray handling apparatus according to the invention.
Figure 2:
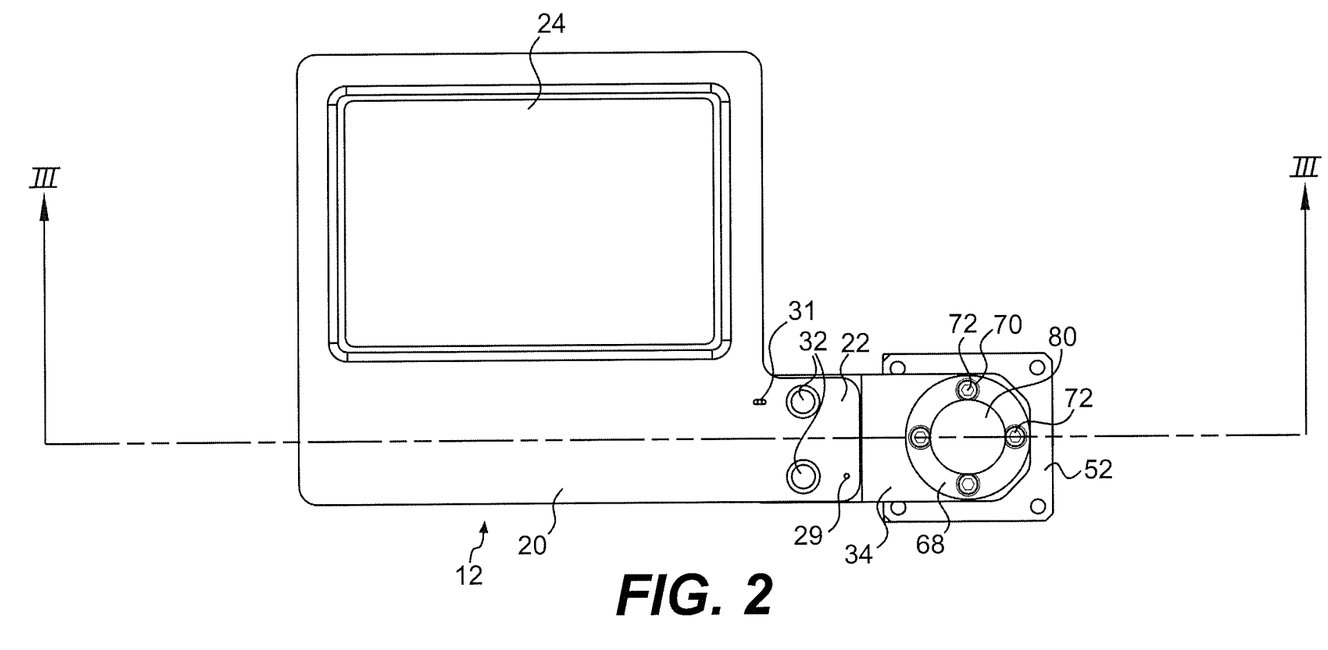
FIG. 2 shows a top view of the sample well tray handling apparatus of FIG. 1.
Figure 3:
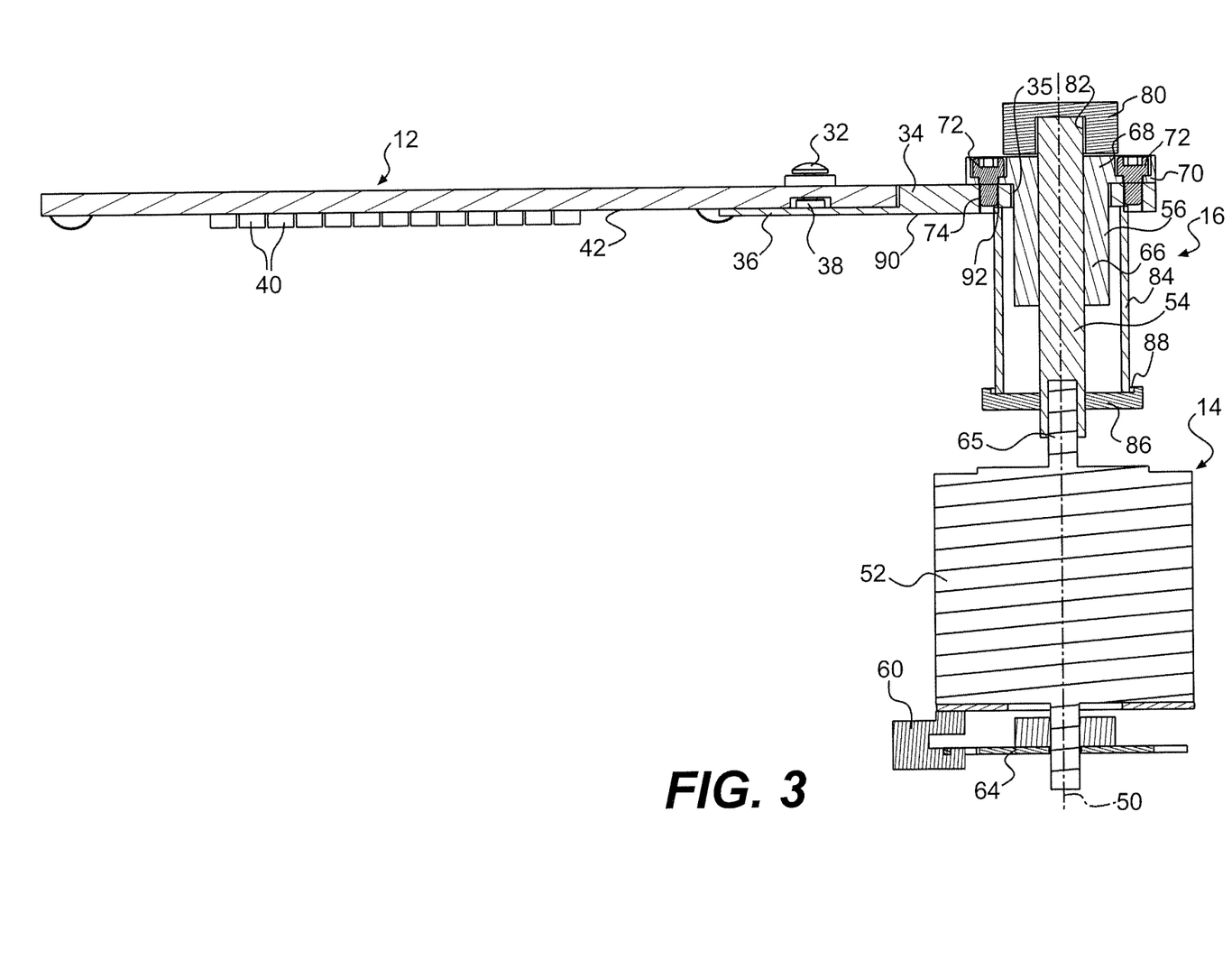
FIG. 3 shows a sectional view of the sample well tray handling apparatus along line III-III of FIG. 2.
Figure 4:
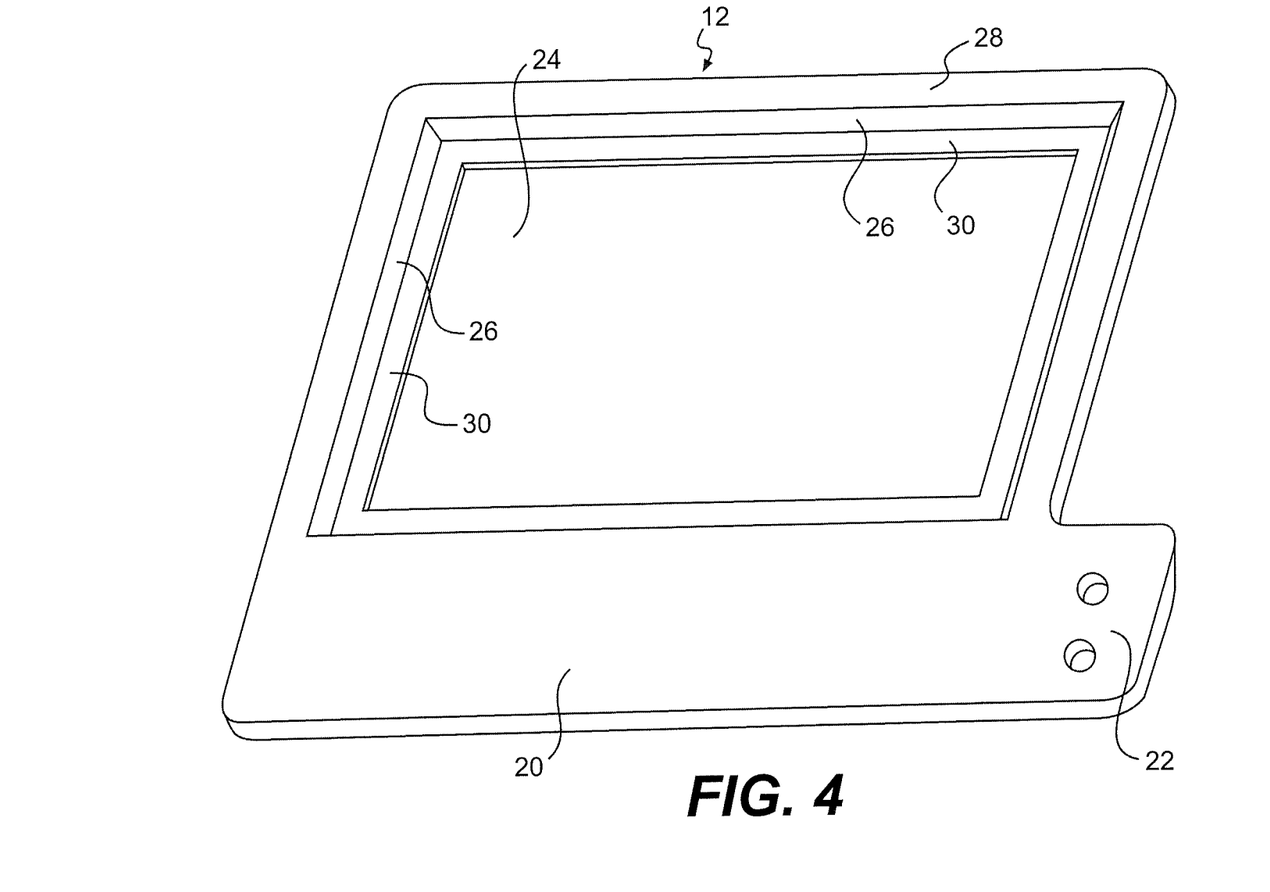
FIG. 4 shows a perspective view of a sample well tray holder of the sample well tray handling apparatus of FIG. 1.

In certain embodiments, the arm portion 22 of the sample well tray holder 12 projects on the same plane as the main body portion 20. In the embodiment shown in FIGS. 1-9, the arm portion includes a plurality of fasteners 32 such as bolts for fastening the sample well tray holder 12 to an extension arm 34 which is connected to the rotational actuator 14 and biasing mechanism 16. As shown in FIG. 3, the extension arm 34 is a flat plate with a thin lower portion 36 on which the arm portion 22 of the sample well tray holder may be mounted. The fasteners 32 pass through the arm portion 22 of the sample well tray holder 12 into a threaded connector 38 on the thin lower portion 36 of the extension arm. The arm portion 22 of the sample well tray holder 12 and the extension arm 34 are preferably configured so that there is minimal movement between the arm portion 22 and extension arm 34. In certain embodiments, the ends of the arm portion 22 and extension arm 34 are flat surfaces that abut against each other as shown in FIG. 2. Additionally, in certain embodiments, the sample well tray holder may include one or more holes to engage with pins in the thin lower portion 36 of extension arm 34. In one embodiment, illustrated for example in FIGS. 1 and 2, the sample well tray holder includes a locating hole 29 and a locating slot 31 for engaging with pins projecting from the top surface of the thin lower portion 36 of extension arm 34. Alternately, the arm portion 22 and extension arm 34 could be an integral piece, thereby reducing the number of parts for the apparatus.

In other embodiments, the connection between the arm portion 22 and extension arm 34 may be configured so that the arm portion 22 is adjustable on the extension arm 34. In such a configurations, the arm portion or extension arm might include two parallel slots for a connector so that the arm distance may be adjusted.

Figure 7:
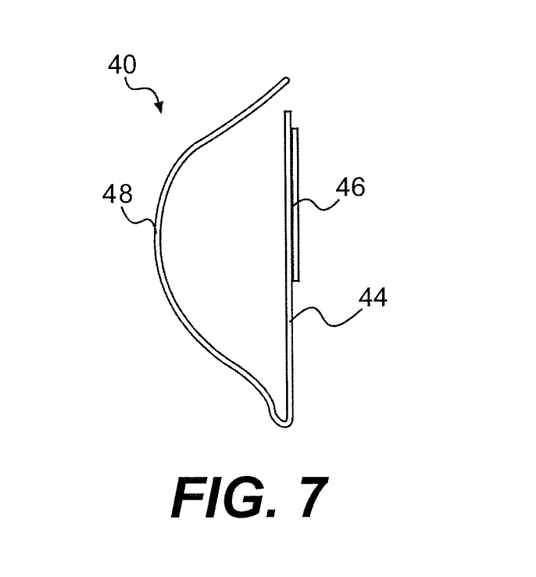
FIG. 7 shows a side view of an urging mechanism positioned on a bottom surface of the sample well tray holder of FIG. 1.
Figure 8:
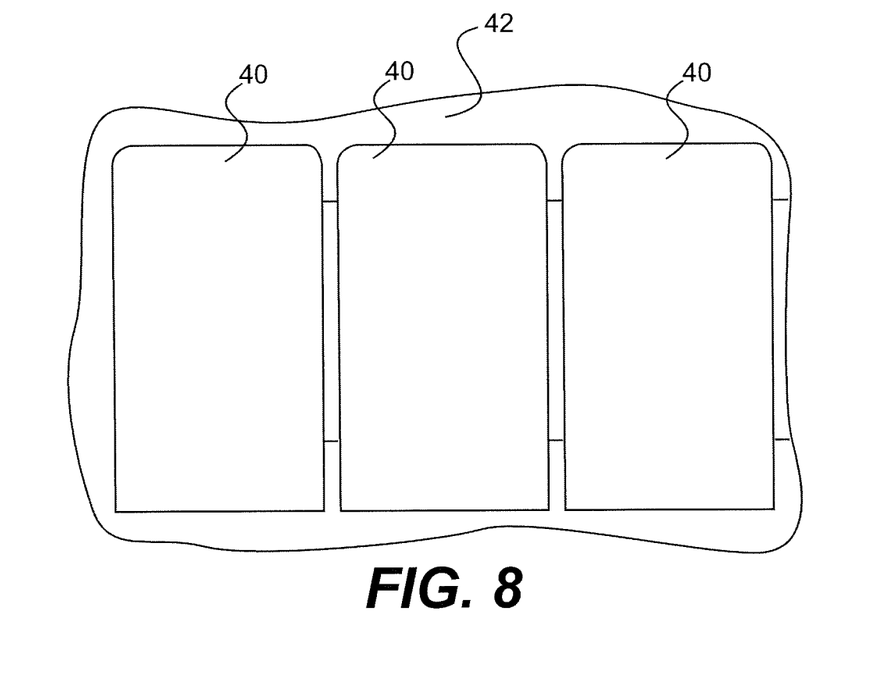
FIG. 8 is a bottom view of the urging mechanism of FIG. 7.

The sample well tray holder 12 may further include an urging mechanism for urging the sample well tray away from the sample block upon opening of the cover. As embodied herein and shown in FIG. 3, the urging mechanism may include any suitable type of mechanism such as a spring device for pressing upward on the sample well tray holder and sample well tray when the cover is opened. In the example shown in FIGS. 1-8, the urging mechanism includes a plurality of springs 40 positioned on the bottom surface 42 of the sample well tray holder 12. As shown in FIGS. 3, 7, and 8, the springs 40, in one example, may be a strip of folded springs commonly referred to as RF gaskets, positioned in parallel relationship to each other. The base 44 of each spring may be attached to the bottom surface 42 of the sample well tray holder 12 by adhesive 46 or any other suitable attachment method. The spring portion 48 of the spring 40 includes a curved member that imparts an upward force on the sample well tray holder 12 when it is compressed.

Although the urging mechanism is shown as being an RF gasket in the figures, any other type of suitable urging mechanism may alternately be used. Examples of other types of urging mechanism are described in co-pending U.S. application Ser. No. 09/496,408, filed Feb. 2, 2000, assigned to the assignee of the present application, the contents of which are hereby incorporated by reference herein. The urging mechanism of the present invention may be made out of any of a variety of force imparting devices such as one or more coil springs, leaf springs, hydraulic dampeners, elastomeric springs, or other conventional spring devices. The urging mechanism is typically designed to provide sufficient force to overcome the sticking force between the sample well tray and the sample block upon opening of the cover of the heating device. Sticking may result because of deformation of the sample well tray during heating. In one example, the urging mechanism imparts an upward force on the sample well tray holder of approximately 15-20 lbs. The amount of force required depends on the specific application. The urging mechanism should preferably loosen the sample well tray from the sample block so that the sample well tray can be easily removed either robotically or manually.

In certain embodiments, particularly those with sample wells having relatively small volumes, it may be desirable to place a thin compliant cover (not shown) between central cover portion 152 and the top of sample well tray 208. An example of a suitable compliant cover is disclosed in the specification and figures (FIGS. 11-13) of co-pending U.S. application Ser. No. 09/499,408, the contents of which are incorporated by reference herein. The compliant cover typically includes detection holes aligned with each of the sample wells 210 of the sample well tray. The compliant cover may assist in evenly distributing the downward force imparted by the cover onto the sample well tray. In embodiments with a compliant cover, it may be helpful to further provide a boss or rib (not shown) on the top surface 28 of the main body portion 20 of sample well tray holder 12 for engaging with the bottom surface of outer cover portion 154 when the outer cover portion 154 is lowered relative to the central cover portion 152. An example of a suitable boss or rib to be used in conjunction with the compliant cover is disclosed in the specification and figures (FIGS. 11-13) of co-pending U.S. application Ser. No. 09/499,408, the contents of which are incorporated by reference herein The downward movement of the outer cover portion 154 results in the outer cover portion 154 pressing downward on the main body portion 20 of sample tray holder 12 so that the upper surface of the floor portion 30 of the sample tray holder will become spaced from the bottom surface 212 of the sample well tray 208. This spacing between the sample well tray and the surface of the floor portion of the sample tray holder isolates the sample well tray 208 from the spring force generated by the springs 40 of the urging mechanism. In certain embodiments, this configuration assists in eliminating the upward force of the springs 40 from the sample tray in order to reduce the amount of volume loss due to bending of the sample tray.

In certain embodiments of the present invention, the handling apparatus 10 removes the sample well tray robotically after the urging mechanism has loosened the sample well tray from the sample block. Alternately, in certain embodiments, urging mechanisms of the type described above could be attached to the sample block instead of the bottom surface of the sample well tray holder. In other embodiments, the urging mechanism may be entirely eliminated because the biasing mechanism 16 (to be described in greater detail later) will provide sufficient force to loosen the sample well tray from the sample block.

In accordance with the present invention, the handling apparatus 10 includes a rotational actuator for rotating the sample well tray holder about a first rotational axis, and a biasing mechanism configured to urge the sample well tray holder in a generally upward direction along the first rotational axis. As embodied herein and shown in FIGS. 1-8, a rotational actuator 14 is provided for rotating the sample well tray about rotational axis 50. As shown in FIGS. 1-9, the rotational actuator 14 includes a motor 52, a spline shaft 54, and a spline bushing 56. The rotational actuator allows the handling apparatus 10 to be rotated about an axis so that the sample well tray may be transported between at least two predetermined positions.

In the example shown in FIGS. 1-9, the motor 52 may be any type of motor capable of providing sufficient force to rotate the sample well tray holder 12 through an approximately 90 degrees rotation. In certain embodiments, the motor is a stepper motor. Other types of rotational force generating devices such as servo motors (with an encoder), rotary solenoids, spring loaded devices, etc. may also be used. In one example, the motor is a 5 volt, 1 amp stepper motor rated at 200 steps per revolution, which may be micro-stepped to provide 1,600 steps per revolution. It is preferable that the motor be controlled accurately so that it provides precise rotation of the sample well tray holder from a first position to a second position, and back to the first position.

In certain embodiments, a rotational position sensing device may be provided in order to enhance the accuracy of the rotational actuator. For example, a rotational position sensing device 58 such as a rotary encoder may be used to control the amount of rotation of the motor. In certain embodiments, the rotational position sensing device includes a sensor 60 that detects the number of slots 62 on a disk 64 that have rotated past the sensor. Other types of rotational position sensing devices are known in the art, and are suitable with the present invention.

As shown in FIG. 3, motor output shaft 65 of motor 52 may be attached to a second shaft such as a spline shaft 54. In the example shown, spline shaft 54 transmits rotational movement to a spline bushing 56 positioned around the spline shaft. The spline shaft 54 transmits rotation to the spline bushing 56 while still allowing relative axial movement between the spline bushing and spline shaft. The spline shaft and bushing are configured so that the spline bushing may move axially along the spline shaft, but remain rotationally fixed to the spline shaft. In certain embodiments, a ball spline and bushing are employed to minimize rotational backlash in the mechanism. Other configurations such as a simple spline configuration with an axial projection and a groove are also suitable with the present invention.

As best shown in FIG. 3, the spline bushing 56 includes an axially extending cylindrical member 66 and a flange member 68 at an end thereof. In the example shown, flange member 68 has an outer diameter greater than the axially extending cylindrical member 66. In certain embodiments, flange member 68 of the spline bushing, which is in the shape of a disk, includes a plurality of holes 70 for receiving bolts to fasten the spline bushing 56 to the extension arm 34. In the embodiment shown in FIGS. 1-8, spline bushing 68 includes four holes 70 through which bolts 72 may pass through into mating holes 74 in the extension arm 34. As shown in FIG. 3, extension arm 34 is configured to include a hole 35 with an inside diameter corresponding to the outside diameter of the axially extending cylindrical member 66 of the spline bushing. Alternately, the extension arm 34 may be attached to the spline bushing by any number of conventional methods, or could be made integral with the spline bushing.

As shown in FIGS. 1-3 and 5-6, a cylindrical stop member 80 is attached to the end of the spline shaft 54. The cylindrical stop member 80 prevents the spline bushing 56 from moving axially along the rotational axis 50 beyond a predetermined point. The cylindrical stop member 80 may be any structure that prevents the spline bushing 56 from moving axially beyond a predetermined point. In the embodiment shown in FIGS. 1-9, the cylindrical stop member is an annular member with an annular recess or counterbore 82 matching the outer diameter of the spline shaft 54. The cylindrical stop member 80 may be attached to the end of the spline shaft 56 by any known method, such as fasteners, threads, interference fit, glue, etc.

The spline bushing may move axially downward on the spline shaft along axis 50. A biasing mechanism 16 is provided to urge the spline bushing in an upward direction to resist movement of the spline bushing in the downward direction in FIG. 3. The biasing mechanism 16 is configured to urge the sample well tray holder 12 and sample well tray 208 away from the sample block 102 when the cover of the heating device 100 is opened. As embodied herein and shown schematically in FIGS. 1 and 3, a spring device such as a helical spring 84 is provided. It should be understood that helical spring 84 is shown schematically for purposes of illustration only. The helical spring may be a variety of sizes and spring constants, depending on the size constraints and the amount of force desired. In one embodiment, the helical spring is approximately 1.75 inches in length, and 1.0 inch in diameter.

In the embodiment of FIGS. 1-9, helical spring 84 is positioned concentric to the rotational axis 50 and surrounds a portion of the length of the spline shaft 54. A bottom annular stop member 86 is positioned on an opposite end of the spline shaft 54 than cylindrical stop member 80. The bottom annular stop member 86 is provided on the spline shaft 54 as shown in FIG. 3, and is in the shape of a disk with an inside bore mating with the outer surface of the spline shaft 54. In the embodiment shown, the annular stop member also includes a counterbore 88 on the top surface thereof for engaging an outer periphery of the bottom portion of the helical spring 84. The counterbore assists in provide a reliable securement of the bottom end of the helical spring. Likewise, the bottom surface 90 of the extension arm 34 includes a counterbore 92 for engaging an outer periphery of the top end of the helical spring 84.

Other types of biasing mechanisms such as elastomeric sleeves may be used instead of helical springs. One or several spring devices such as leaf springs, conical helical springs, elastomers, and other springs which impart an axial force when compressed are also suitable with the present invention. In addition, other spring-like devices suitable for use in the present invention include, for example, air cylinders, fluid cylinders, dampeners, belleville washers, and electrical solenoids. The size and type of spring device depend on the specific design constraints of the handling apparatus.

Helical springs, also called coil springs, such as shown in the figures are particularly suitable in applications where relatively large compression stroke lengths are desired, whereas an elastomeric sleeve may be suitable if short compression stroke lengths are preferred. In one example, the helical spring 84 is compressed about 0.5 inches. In applications with a large compression stroke for the biasing mechanism, a helical spring may be better suited than an elastomeric sleeve. The biasing mechanism is typically configured so that the sample well tray may be pushed downward a slight distance by the cover of the heating device after the sample well tray is aligned with the sample block. As shown for example in FIG. 9B, the cover 150 of the heating device typically presses downward on the sample well tray 208 so that the sample wells 210 of the sample well tray are firmly pressed against surfaces of the sample block openings 104 in the sample block 102.

As the sample well tray holder is pressed downward, the helical spring 84 is compressed a slight distance. Because the spring constant of the helical spring is small relative to the downward force of the cover, the upward force imparted by the helical spring will not bend the sample well tray. The force imparted by the helical spring of the biasing mechanism will be sufficient to lift the loosened sample well tray away from the sample block, after the urging mechanism has loosened the sample wells from the sample block openings, so that the bottoms of the sample wells 210 do not interfere with the corresponding openings 104 in the sample block. FIG. 9A shows the position of the sample well tray after the biasing mechanism lifts the sample well tray from the sample block. In one example, the biasing mechanism imparts an upward force of approximately six lbs on the sample well tray holder. The biasing mechanism cooperates with the springs 40 of the urging mechanism to lift the sample well tray completely out of the sample block recesses after the springs 40 of the urging mechanism have overcome the sticking force between the sample wells and the sample block.

The operation of the handling apparatus for one typical embodiment corresponding to FIGS. 1-9 will now be more completely described below. First, a robot such as rotational robot 200 shown in FIG. 5 grasps a sample well tray 208 with a grasper such as robot hand 206. The robot arm 204 and robot hand 206 then rotate the sample well tray about rotational axis 202 to the position shown in FIG. 5. The rotational robot 200 opens robot hand 206 to drop the sample well tray 208 into the rectangular opening 24 of the sample well tray holder 12 of the handling apparatus 10. As shown in FIG. 5, the handling apparatus 10 is located in a first position so that the rectangular opening 24 is aligned with the sample well tray 208 in the robot hand 206. Preferably, the rectangular opening 24 includes tapered walls so that the sample well tray 208 slides downward into the rectangular opening 24 of sample well tray holder 20 and is centered in the rectangular opening.

After the sample well tray 208 is seated in the rectangular opening 24 of the sample well tray holder 12, the rotational actuator 14 of the handling apparatus 10 rotates the sample well tray holder 12 about rotational axis 50 from a first position shown in FIG. 5 to a second position shown in FIG. 6. In the rotational actuator described above, for example, motor 52 rotates motor output shaft 65 and spline shaft 54. Spline shaft 54 transmits torque to spline bushing 56 and extension arm 34. The extension arm 34 is connected to arm portion 22 of sample well tray holder 12 and transmits rotational motion to the sample well tray holder 12. The sample well tray holder 12 is thereby rotated approximately ninety degrees about rotational axis 50 from the first position shown in FIG. 5 to a second position shown in FIG. 6. This is a clockwise rotation as viewed in FIGS. 5 and 6.

At the second position shown in FIG. 6, the sample well tray 208 is roughly aligned with the sample block 102 of heating device 100. Each of the plurality of sample wells 210 of the sample well tray are aligned with a respective opening 104 in the sample block, as shown for example in FIG. 9A. The sample well tray 208 is initially positioned over the sample block 102 at a first height so that the sample wells of the sample well tray have clearance over the sample block so that the sample well tray holder can be swung into position. This initial position is shown for example in FIG. 9A.

A cover 150 of the heating device, initially positioned over the sample well tray may then be lowered, pressing against the top surface of the sample well tray and sample well tray holder so that the sample wells of the sample well tray 208 are lightly pressed against the recesses of the sample block 102. As the sample well tray holder lowers to this second height, the helical spring 84 of the biasing mechanism 16 is compressed. The spline bushing 56 is thereby lowered so that a space is created between the top of the spline bushing and the bottom surface of stop member 80. As the cover 150 continues to be lowered, the springs 40 of the urging mechanism are then compressed until the sample well tray holder 20 reaches a third height shown in FIG. 9B, and the cover is completely closed. At this third height shown in FIG. 9B, the sample wells 210 of the sample well tray 208 are firmly pressed against the openings 104 of the sample block.

The heating device, such as thermal cycler 100, thereafter heats the liquid sample in the sample well tray to undergo a PCR or other type of chemical reaction. After the thermal cycling and/or other operations are completed, the cover 150 is opened. As the cover is opened, the cover will no longer press against the top of the sample well tray. Simultaneously, the springs 40 of the urging mechanism will impart an upward force on the bottom surface 42 of the sample well tray, thereby urging the sample wells 210 upward so that they no longer press against the surface of the openings 210 of the sample block. The springs should impart sufficient force so that the sample well tray becomes loosened from the sample block. At this second height, the sample wells are still positioned in the recesses in the sample block, consequently, the sample well tray holder cannot be rotated away from the sample block without interfering with the sample block.

The provision of the biasing mechanism 16 permits for the immediate raising of the sample well tray out of the sample block above the second height. Helical spring 84 of biasing mechanism 16 presses upward on the spline bushing 56 so that the sample well tray holder returns to its first height (FIG. 9A). At the first height, the top of the spline bushing 56 typically abuts a bottom surface of the stop member 80. The first height corresponds to a height at which the sample well tray can be rotated away from the sample block without interference. This is shown for example in FIG. 9A. Consequently, the sample well tray holder 12 can now be rotated from the second position shown in FIG. 6 to the first position shown in FIG. 5 by the rotational actuator. The rotational actuator rotates the sample well tray holder in the opposite direction (counterclockwise as viewed in FIGS. 5 and 6) as it was previously rotated. When the sample well tray holder and sample well tray are returned to the first position shown in FIG. 5, the robot hand 206 of the robot 200 may grasp the sample well tray 208 and remove it from the sample well tray holder 12. Thereafter, the robot 200 may rotate and bring the sample well tray to a receiving position, for example, a position on the robot. The robot 200 may then grab another sample well tray on or adjacent the robot, within the radius of the robot arm, and repeat the above operation.

As is clear from the above description, the present invention includes a method of manipulating sample well trays. The method includes the step of placing the sample well tray into a sample well tray holder of a first robot mechanism located at a first position. The method further includes the step of rotating the sample well tray holder of the first robot mechanism about a rotational axis in a first rotational direction to insert the sample well tray holder into a heating device at a second position. The sample well tray engages with a cover of the heating device to lower the sample well tray holder in a direction toward a sample block of the heating device so that the sample wells of the sample well tray firmly engage the corresponding openings in the sample block. The sample well tray then undergoes a heating operation such as thermal cycling. After the heating operation is completed, the cover of the heating device is opened so that the sample well tray and sample wells disengage from the sample block. As a result, the sample well tray no longer directly contacts the sample block. The method further includes lifting the sample well tray holder and sample well tray from the sample block openings by a biasing mechanism so that the sample well tray is capable of rotation away from the sample block and heating device without interference. The sample well tray holder is then rotated in a second rotational direction toward the first position to remove the sample well tray holder from the heating device. The method further comprises, prior to placing the sample well tray in a sample well tray holder, the steps of picking up a sample well tray with a second robot mechanism, such as a rotational robot, and rotating the sample well tray to place the sample well tray in the first position.

The system and method according to the present invention may be used to transport a large number of sample well trays into a thermal cycler having detection capabilities. This may increase throughput and improve safety for operators of thermal cyclers. With such a handling apparatus, it is unnecessary to manually load the sample well trays into a thermal cycler.

It will be apparent to those skilled in the art that various modifications and variations can be made in the apparatus and method for handling sample well trays, use of the apparatus of the present invention, and in construction of this apparatus, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for manipulating and thermal cycling a sample well tray, comprising:
   a sample block for receiving a sample well tray, the sample block comprising a plurality of openings for receiving sample wells of the sample well tray; and
   a sample well tray handling apparatus comprising:
      a sample well tray holder comprising a locating hole and a locating slot and configured to receive the sample well tray therein;
      a biasing member configured to urge the sample well tray and sample well tray holder in a direction away from the sample block;
      an extension arm comprising pins projecting upward and configured to mate with the locating hole and locating slot of the sample well tray holder and fixed to the sample well tray holder with a plurality of fasteners,
   wherein the sample well tray handling apparatus is configured to move the sample well tray from a first location distal to the sample block to a second location proximal to the sample block and then later remove the sample well tray from the second location to the first location; and
   a cover comprising a plurality of openings and configured to press the sample well tray against the sample block when the sample well tray is moved to the second position.

2. The system of claim 1, wherein, at the first location, the sample well tray is accessible by a robot.

3. The system of claim 1, further comprising a detection unit configured to provide a real-time detection capability during thermal cycling at the second location, wherein operation of the sample well tray handling apparatus does not interfere with the detection unit.

4. The system of claim 1, wherein the biasing member comprises a spring.

5. The system of claim 1, further comprising a robot with a robotic arm configured to transport the sample well tray from a third location distal to the sample block to the first location.

6. The system of claim 5, wherein the robotic arm is rotatable between the third location and the first location with respect to a second rotational axis.

7. The system of claim 1, further comprising a sensor for sensing a rotational position of the sample well tray holder.

8. The system of claim 1, wherein the rotational angle between the first position and the second position with respect to the rotational axis is approximately 90 degrees.

9. A system for manipulating and thermal cycling a sample well tray, comprising:
   a thermal cycling device comprising a sample block for receiving a sample well tray, the sample block comprising a plurality of openings for receiving sample wells of the sample well tray; and a sample well tray handling apparatus comprising:
- a sample well tray holder comprising a locating hole and a locating slot and configured to receive the sample well tray therein;
- a biasing member configured to urge the sample well tray and sample well tray holder in a direction away from the sample block;
- an extension arm comprising pins projecting upward and configured to mate with the locating hole and locating slot of the sample well tray holder and connected to the sample well tray holder with a plurality of fasteners,
- wherein the sample well tray handling apparatus is configured to move the sample well tray from a first location distal to the sample block to a second location proximal to the sample block and then later remove the sample well tray from the second location to the first location; and
- a cover comprising at least one heated platen and configured to press the sample well tray against the sample block when the sample well tray is moved to the second position.

10. The system of claim 9, wherein, at the first location, the sample well tray is accessible by a robot.

11. The system of claim 9, further comprising a detection unit configured to provide a real-time detection capability during thermal cycling at the second location, wherein operation of the sample well tray handling apparatus does not interfere with the detection unit.

12. The system of claim 9, wherein the biasing member comprises a spring.

13. The system of claim 9, further comprising a robot with a robotic arm configured to transport the sample well tray from a third location distal to the sample block to the first location.

14. The system of claim 13, wherein the robotic arm is rotatable between the third location and the first location with respect to a second rotational axis.

15. The system of claim 9, further comprising a sensor for sensing a rotational position of the sample well tray holder.

16. The system of claim 9, wherein the rotational angle between the first position and the second position with respect to the rotational axis is approximately 90 degrees.

* * * * *